United States Patent
Uusimaa et al.

(10) Patent No.: US 12,343,558 B2
(45) Date of Patent: Jul. 1, 2025

(54) METHOD FOR LIGHT-ACTIVATED DRUG DELIVERY AND SYSTEM

(71) Applicant: Modulight, Inc., Tampere (FI)

(72) Inventors: Petteri Uusimaa, Tampere (FI); Robert Perttilä, Tampere (FI); Sallamaari Ylöniemi, Tampere (FI)

(73) Assignee: Modulight, Inc., Tampere (FI)

( * ) Notice: Subject to any disclaimer, the term of this patent is extended or adjusted under 35 U.S.C. 154(b) by 813 days.

(21) Appl. No.: 17/392,388

(22) Filed: Aug. 3, 2021

(65) Prior Publication Data

US 2023/0041277 A1      Feb. 9, 2023

(51) Int. Cl.
*A61N 5/06*      (2006.01)

(52) U.S. Cl.
CPC ...... *A61N 5/062* (2013.01); *A61N 2005/0628* (2013.01); *A61N 2005/0662* (2013.01)

(58) Field of Classification Search
CPC .... A61N 2005/0628; A61N 2005/0662; A61N 5/062; A61B 18/22
See application file for complete search history.

(56) References Cited

U.S. PATENT DOCUMENTS

| | | |
|---|---|---|
| 10,588,514 B1 | 3/2020 | Shang |
| 2016/0022976 A1 | 1/2016 | Peyman |
| 2017/0224205 A1* | 8/2017 | Sunar .................. A61B 1/0684 |

FOREIGN PATENT DOCUMENTS

| | | |
|---|---|---|
| WO | 9906113 A1 | 2/1999 |
| WO | 2015089154 A1 | 6/2015 |

OTHER PUBLICATIONS

European Patent Office, Written Opinion of the International Searching Authority, dated Oct. 28, 2022, 7 pages.

* cited by examiner

*Primary Examiner* — Scott Luan
(74) *Attorney, Agent, or Firm* — Ziegler IP Law Group, LLC.

(57) ABSTRACT

A method and a system for light-activated drug delivery. An optical probe is coupled to a tissue for transmitting light signals to the tissue for actuating and/or monitoring drug delivery with a multi-phase method for drug delivery. A first light signal is transmitted through the optical probe for actuating and/or monitoring the drug delivery and a second light signal having a different wavelength is transmitted, simultaneously with the first light signal, through the optical probe for actuating and/or monitoring the drug delivery.

20 Claims, 4 Drawing Sheets

METHOD FOR LIGHT-ACTIVATED DRUG DELIVERY AND SYSTEM

FIELD

The present disclosure relates to light-activated drug delivery. In particular, it can be utilized in the field of oncology and treatment of cancer with photoactive drugs, photosensitizers and/or drug-delivery constructs with photoactive parts.

BACKGROUND

Medical lasers are used, for example, in operating room and sterile conditions. Therapeutic or hard tissue illumination provided by the medical laser may be combined with treatment monitoring functions to provide a theranostic medical device. It would be beneficial to improve drug delivery process with theranostic medical devices.

SUMMARY

This summary is provided to introduce a selection of concepts in a simplified form that are further described below in the detailed description. This summary is not intended to identify key features or essential features of the claimed subject matter, nor is it intended to be used to limit the scope of the claimed subject matter.

The solutions disclosed herein combine functionalities of therapeutic laser systems with some properties of diagnostic/monitoring devices. The solutions can be used with light-activated drug delivery constructs, such as nano-constructs. These may comprise or consist of a carrier, such as a liposome, an encapsulated drug and/or targeting component within the carrier, and a light-activated component/photosensitizer. A drug delivery system can be configured for simultaneously facilitating the actuation of a therapeutic effect and monitoring various processes during such treatment by utilizing fluorescence and/or other optical imaging solutions for components of the drug-delivery construct.

It is disclosed a low-invasive solution which can be used for not only inducing the multi-phase therapeutic drug delivery effect but additionally or alternatively for monitoring multiple processes happening during photodynamic therapy (PDT), photochemotherapy treatment or other light-utilizing treatment modality. The solutions allow utilization of standard light-activation illumination fibers also for monitoring interstitial processes eliminating the need of introducing any unnecessary foreign objects to the tissue to minimize mechanical stress caused to the tissue.

The disclosed solutions may be used in oncology to allow a clinician more precisely illuminate a tumor as a whole and monitor progress during a treatment. This functionality may markedly increase the odds for success for light-activated therapies, in particular by allowing real-time feedback from the tumor environment. The previously introduced treatment monitoring solutions for PDT, photoimmunotherapy (PIT) or other light-activated drug delivery methods are typically based on using separate probes or cameras for optical monitoring purposes. The disclosed solutions may be utilized with an all-fiber single multi-purpose probe for treatment delivery and monitoring and allow simultaneous treatment activation and monitoring real-time and independent of each other without separate switching between the different modalities (in particular of treatment and monitoring). The solutions further support separation of different optical signals, which may be represented by different wavelengths, at a monitoring device by applying a wavelength-sensitive detection unit.

The solutions may involve simultaneous treatment and real-time monitoring of multi-phase drug delivery, which may comprise one or more phases during treatment such as any of the following, alone or in any combination: drug carrier arrival to tissue, drug release from carrier, drug activation (which may include activation of a separate photo-activated drug and/or a photosensitizer, completion of the drug activation, detecting an obstruction such as a blood flow during the treatment, and change in the tissue optical properties, for example due to heat and/or ablation.

The solutions may allow combining targeted chemotherapeutic drug delivery, local tumor control via PIT and immunogenic long-lasting antitumor effect. They may also allow generic diagnosis, imaging and/or treatment technology for theranostics. They can be used for targeting all three major components of a cancer cell: plasma membrane (e.g. with antibody), cytoplasm (e.g. with photosensitizer) and/or nucleus (e.g. with chemo). Nanoliposome carrier may improve photo-immunoconjugate (PIC) uptake into cancer cells by enabling co-delivery of multiple photo-immunoconjugates. Light-activation may be used to boost efficacy of chemotherapy and may sensitize drug resistant tumor cells to chemo. The solutions may also be used for inducing immunotherapeutic systemic and long-lasting antitumor response.

According to a first aspect, a method for light-activated drug delivery is disclosed. The method may comprise coupling an optical probe to a tissue for transmitting light signals to the tissue for actuating and/or monitoring drug delivery. Importantly, the method may be a multi-phase method for drug delivery having two or more sequential actuation and/or monitoring phases for the drug delivery. The method may comprise causing a first light signal having a first wavelength to be transmitted through the optical probe for actuating and/or monitoring the drug delivery. The method may also comprise causing a second light signal having a second wavelength to be transmitted, simultaneously with the first light signal, through the optical probe for actuating and/or monitoring the drug delivery. Importantly, the first wavelength can be different from the second wavelength.

In an embodiment, the first light signal is transmitted to the tissue and the second light signal is received from the tissue to monitor the arrival of a drug-delivery construct, or a drug, to the tissue.

In an embodiment, the first light signal is transmitted to the tissue and the second light signal is received from the tissue to monitor the integrity of a drug-delivery construct, for example a carrier encapsulating a drug, for drug delivery.

In an embodiment, the first light signal is transmitted to the tissue to actuate the drug delivery by inducing a release of a drug from a carrier and the second light signal is received from the tissue to monitor the release.

In an embodiment, the first light signal is transmitted to the tissue to actuate the drug delivery by inducing an activation of a drug and the second light signal is received from the tissue to monitor the activation.

In an embodiment, the first light signal is transmitted to the tissue for probing an activation of a drug and the second light signal is received from the tissue for monitoring a completion of the activation of a drug.

In an embodiment, the first light signal is transmitted to the tissue to activate fluorescence from a drug and/or a drug-delivery construct and the second light signal is received from the tissue to monitor the fluorescence.

In an embodiment, the first light signal is transmitted to the tissue to activate a characteristic optical response, like fluorescence, reflectance or Raman scattering signal or alike, from the tissue and the second light signal is received from the tissue to monitor the characteristic optical response.

In an embodiment, the method comprises causing one or more signals having a different wavelength to be transmitted simultaneously with the first signal and the second signal through the optical probe for actuating and/or monitoring the drug delivery, the different wavelength being different from the first wavelength and the second wavelength.

In an embodiment, two or more different wavelengths are used for actuating drug delivery or two or more different wavelengths are used for inducing a monitoring signal.

In an embodiment, two or more different wavelengths are used for monitoring drug delivery.

According to a second aspect, a light-activated drug delivery system is disclosed. The system may comprise a light source for providing light signals for actuating and/or monitoring drug delivery. The system may also comprise an optical probe coupled to the light source for transmitting the light signals to a tissue for actuating and/or monitoring drug delivery and for transmitting light signals from the tissue for monitoring the drug delivery. The system may comprise a light receiver coupled to the optical probe for receiving the light signals from the tissue for monitoring the drug delivery. Importantly, the system can be configured for multi-phase drug delivery with two or more sequential actuation and/or monitoring phases. The system may also be configured for causing a first light signal having a first wavelength to be transmitted through the optical probe for actuating and/or monitoring the drug delivery. The system may be configured for causing a second light signal having a second wavelength to be transmitted, simultaneously with the first light signal, through the optical probe for actuating and/or monitoring the drug delivery. Importantly, this can be in a manner that the first wavelength is different from the second wavelength.

In an embodiment, the system can be configured to monitor an arrival of a drug to the tissue by transmitting the first light signal to the tissue and receiving the second light signal from the tissue.

In an embodiment, the system can be configured to monitor the integrity of a carrier encapsulating a drug for drug delivery by transmitting the first light signal to the tissue and receiving the second light signal from the tissue.

In an embodiment, the system can be configured to actuate the drug delivery by transmitting the first light signal to the tissue to induce a release of a drug from a carrier, and receive the second light signal from the tissue to monitor the release.

In an embodiment, the system can be configured to actuate the drug delivery by transmitting the first light signal to the tissue to induce an activation of a drug and receive the second light signal from the tissue to monitor the activation.

In an embodiment, the system can be configured to monitor completion of activation of a drug by transmitting the first light signal to the tissue and receiving the second light signal from the tissue.

In an embodiment, the system can be configured to monitor the drug delivery by transmitting a first light signal to the tissue to activate fluorescence from a drug and/or a drug-delivery construct, and receiving the second light signal to monitor the fluorescence.

In an embodiment, the system can be configured to monitor a characteristic optical response from the tissue by transmitting a first light signal to the tissue to induce a characteristic optical response, like fluorescence, reflectance or Raman scattering signal, from the tissue, and receiving the second light signal to monitor the characteristic optical response from the tissue.

In an embodiment, the system can be configured for causing one or more signals having a different wavelength to be transmitted simultaneously with the first signal and the second signal through the optical probe for actuating and/or monitoring the drug delivery, the different wavelength being different from the first wavelength and the second wavelength.

In an embodiment, the system can be configured for simultaneously transmitting two or more light signals having different wavelengths through the optical probe for actuating drug delivery and/or for simultaneously transmitting two or more light inducing a monitoring signal. In an embodiment, the system comprises a wavelength-sensitive detection unit for simultaneously monitoring two or more different wavelengths received through the optical probe for monitoring drug delivery.

It is to be understood that the aspects and embodiments described above may be used in any combination with each other. Several of the aspects and embodiments may be combined together to form a further embodiment of the present disclosure.

Some of the effects that may be obtained with the present solutions include: real-time monitoring of drug delivery (in contrast to prescribed intervals), monitoring multiple dyes or photosensitizers (e.g. with multiple wavelengths), applicability for multi-phase treatments, and no need to use switches and/or shutters or separate fibers for detection channels. A single laser source can also be used both as a treatment beam and for monitoring, for example for detection and/or activation monitoring excitation light such as fluorescence light. The present solutions can be used for light dosimetry. They may be used for in-situ monitoring of tissue. They also allow collecting spectral point information at several locations in a tissue simultaneously. Monitoring may be performed with a single spectrometer, in contrast to using multiple ones. Monitoring may be based on spectral information. The solutions may be implemented as multi-channel and/or multi-wavelength solutions.

The solutions, for example implemented at a theranostic laser device, can both induce a therapeutic effect of a treatment and monitor different processes taking place during the treatment. They may utilize the same optical probes, such as optical fibers, for both processes without need to insert separate monitoring devices around the treated tissue area or switch between treatment fibers and monitoring probes at selected locations. The solutions enable usage of one or more lasers with one or more wavelengths for a drug delivery construct to activate treatment or excite an optical monitoring process. Different components of a drug delivery construct can be optically monitored freely in parallel without need for switching between different functions of each delivery channel. Multiple illumination wavelengths can be coupled into single optical fiber probe that is inserted into tissue without any physical or optical switching between different functions. This makes it possible to do treatment and monitoring simultaneously and thus get real-time information about the treatment progress. This information about different interstitial processes during the treatment can be collected to a remote processing system such as a cloud. It can be analyzed locally or remotely for treatment decision making. The very same probes inserted into the tissue can be also used for collecting optical signals, possibly with different wavelengths, from the tissue to monitor different drug delivery processes in-situ when delivering the treatment.

BRIEF DESCRIPTION OF THE DRAWINGS

The accompanying drawings, which are included to provide a further understanding and constitute a part of this specification, illustrate examples and together with the description help to explain the principles of the disclosure. In the drawings.

Like references are used to designate equivalent or at least functionally equivalent parts in the accompanying drawings.

DETAILED DESCRIPTION

The detailed description provided below in connection with the appended drawings is intended as a description of examples and is not intended to represent the only forms in which the example may be constructed or utilized. However, the same or equivalent functions and structures may be accomplished by different examples.

Figure 1:
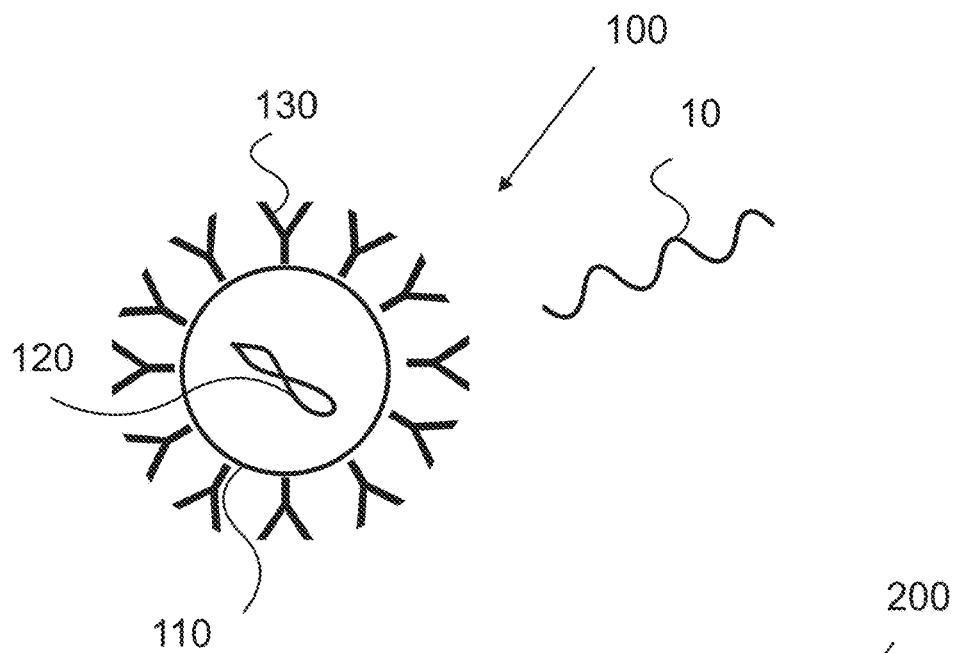
FIG. 1 illustrates a drug-delivery construct according to an example.

FIG. 1 shows an example of a drug-delivery construct 100 for multi-phase drug delivery. The drug delivery construct may be a nanoconstruct. It may comprise or consist of a carrier 110, one or more drugs and/or targeting components 120 within the carrier, and one or more light-activated components, such as photosensitizers. The carrier may comprise or consist of a liposome, such as a nanoliposome. It can encapsulate the one or more drugs and/or targeting components. The one or more drugs may comprise or consist of, for example, one or more chemotherapeutic drugs, such as Irinotecan. One or more elements 130 may be coupled to the carrier for multi-phase drug-delivery. These elements may comprise antibodies and/or photosensitizers. The antibodies may be, for example, EGFR-targeted antibodies such as Cetuximab. The photosensitizer may be, for example benzoporphyrin derivative (BPD). The photosensitizers may be coupled to the antibodies, for example on the surfaces of the antibodies. The one or more elements may thereby comprise antibody-conjugated photosensitizers, e.g. BPD+Cetuximab. The drug delivery may be actuated by light 10 such as laser light, for example near-infrared laser light. The actuation, wherever referred, may comprise activation of a drug, such as a photoactive drug, and/or a photosensitizer, for example by a photodynamic reaction. Additionally or alternatively, it may comprise enhancing the efficacy of a drug.

Figure 3:
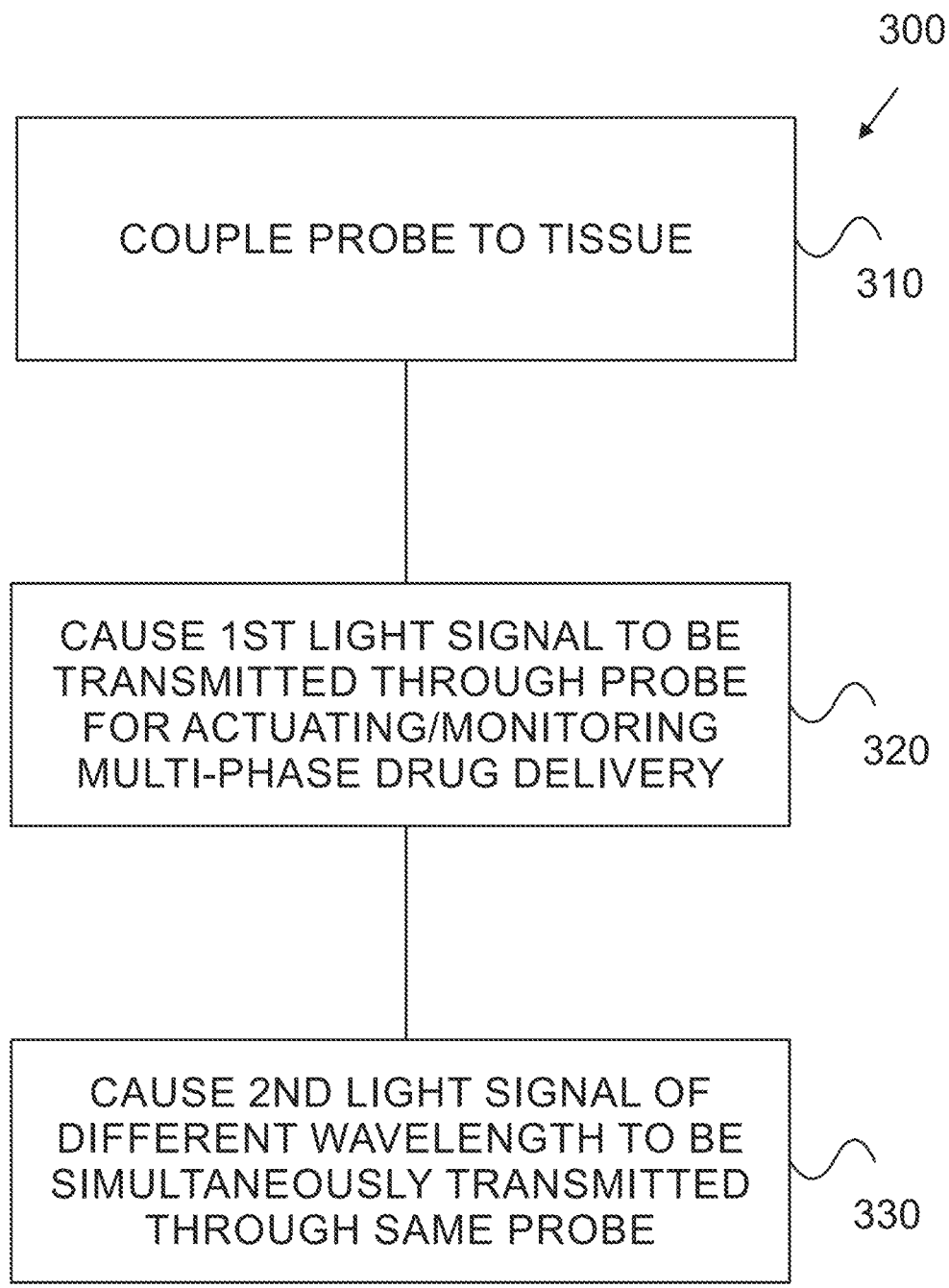
FIG. 3 illustrates a method according to an example.

FIG. 3 shows an example of a method 300, which may be used for light-activated drug delivery. The method may comprise coupling 310 an optical probe to a tissue for transmitting light signals to the tissue for actuating and/or monitoring drug delivery. The optical probe may comprise or consist of an optical fiber. The optical probe may be coupled to the tissue for in-situ delivery of light to the tissue and/or in-situ receipt of light from the tissue. The coupling may be substantially non-invasive.

The method may be a multi-phase method for drug delivery. It may involve drug delivery with the drug-delivery construct 100 in accordance with what has been disclosed herein. The multi-phase method for drug delivery may have two or more sequential actuation and/or monitoring phases for the drug delivery. In some embodiments, there may be two or more sequential actuation phases for the drug delivery. Alternatively or additionally, there may be two or more sequential monitoring phases for the drug delivery. Two or more phases, including actuation and/or monitoring phases, may also be performed simultaneously for the drug delivery. The actuation phases may comprise, for example, activation of a drug, activation of a photosensitizer and/or enhancement of efficacy of a drug. The monitoring phases may comprise, for example, actuating response from one or more targets such as dyes, fluorescence labels and/or photosensitizers. They may also comprise receiving any such response. The monitoring phases may also comprise activating a characteristic optical response, like fluorescence, reflectance or Raman scattering signal or alike, from the tissue itself. They may also comprise receiving any such response. All of the aforementioned alternatives may be facilitated by delivering light to the tissue through the optical probe. In particular, the same optical probe may be used for any combination of the alternatives. Two or more of the alternatives, regardless of whether they involve actuating or monitoring the drug delivery, may be performed simultaneously utilizing the same probe.

The method 300 may comprise causing 320 a first light signal having a first wavelength to be transmitted through the optical probe for actuating and/or monitoring the drug delivery. The method may also comprise causing 330 a second light signal having a second wavelength to be transmitted, simultaneously with the first light signal, through the optical probe for actuating and/or monitoring the drug delivery. Importantly, the first wavelength can be different from the second wavelength. The light signals, including the first light signal and/or the second light signal, may be light pulses. A single pulse may consist substantially of single wavelength or of multiple separate wavelengths. They may be of any appropriate frequency, for example visible light, infrared or near-infrared frequency. They may be provided by a laser source, for example a near-infrared laser source.

The first light signal may be a signal transmitted to the tissue for actuating and/or monitoring drug delivery. The second light signal may be a signal transmitted from the tissue for monitoring the drug delivery. On the other hand, the first light signal and the second light signal may both be signals transmitted to the tissue for actuating and/or monitoring drug delivery or they may both be signals transmitted from the tissue for monitoring the drug delivery. The method may also comprise receiving two or more light signals from the optical probe at a wavelength-sensitive detection unit for distinguishing said light signals based on their wavelength.

The method may comprise several additional parts which may be performed independently from each other and/or in any order. For example, the first light signal may be transmitted to the tissue to monitor the arrival of a drug-delivery construct, or a drug, to the tissue. Alternatively or additionally, the second light signal may be received from the tissue for this purpose. The first light signal may also be transmitted to the tissue to monitor the integrity of a drug-delivery construct, for example a carrier encapsulating a drug, for drug delivery. Alternatively or additionally, the second light signal may be received from the tissue for this purpose. The first light signal may be transmitted to the tissue to actuate the drug delivery by inducing a release of a drug from a carrier. Alternatively or additionally, the second light signal may be received from the tissue to monitor the release. The first light signal may be transmitted to the tissue to actuate the drug delivery by inducing an activation of a drug.

Alternatively or additionally, the second light signal may be received from the tissue to monitor the activation. The first light signal may be transmitted to the tissue for probing an activation of a drug. Alternatively or additionally, the second light signal may be received from the tissue for monitoring a completion of the activation of a drug. For example, the strength of the second light signal dropping below a threshold level or the second light signal disappearing altogether may be determined as an indication of completion of the activation.

All of the above examples may utilize fluorescence for the monitoring. The drug-delivery construct may comprise one or more fluorescence markers for this purpose. It may also comprise two or fluorescence markers corresponding to different fluorescence wavelengths. The first light signal may be transmitted to the tissue to activate fluorescence from a drug and/or a drug-delivery construct. Alternatively or additionally, the second light signal may be received from the tissue to monitor the fluorescence. The first light signal may be transmitted to the tissue to activate a characteristic optical response, like fluorescence, reflectance or Raman scattering signal or alike, from the tissue itself. Alternatively or additionally, the second light signal may be received from the tissue to monitor the characteristic optical response from the tissue itself.

The method 300 may comprise causing one or more signals having a different wavelength to be transmitted simultaneously with the first signal and the second signal through the optical probe for actuating and/or monitoring the drug delivery, the different wavelength being different from the first wavelength and the second wavelength. The number of different wavelengths is not necessarily limited and can well be 5-10, for example. Two or more different wavelengths may be used for actuating drug delivery, for example for two different drugs and/or for two different photosensitizers. Two or more different wavelengths may also be used for inducing a monitoring signal, for example for two different targets, such as fluorescence markers. Alternatively or additionally, two or more different wavelengths may be used for monitoring drug delivery, both for actuating the monitoring, for example by actuating a target such as a fluorescence marker or by monitoring two or more different wavelengths from the tissue.

All of the above steps may be performed simultaneously and in any combination. For this purpose, the same optical probe may be used. Correspondingly, no switching between sending and receiving is required, nor is required the use of multiple probes, although multiple probes may still be used for various purposes. For example multiple different wavelengths through the same optical probe may be simultaneously used for actuating the drug delivery and/or multiple different wavelengths through the same optical probe may be simultaneously used for monitoring the drug delivery.

Figure 4:
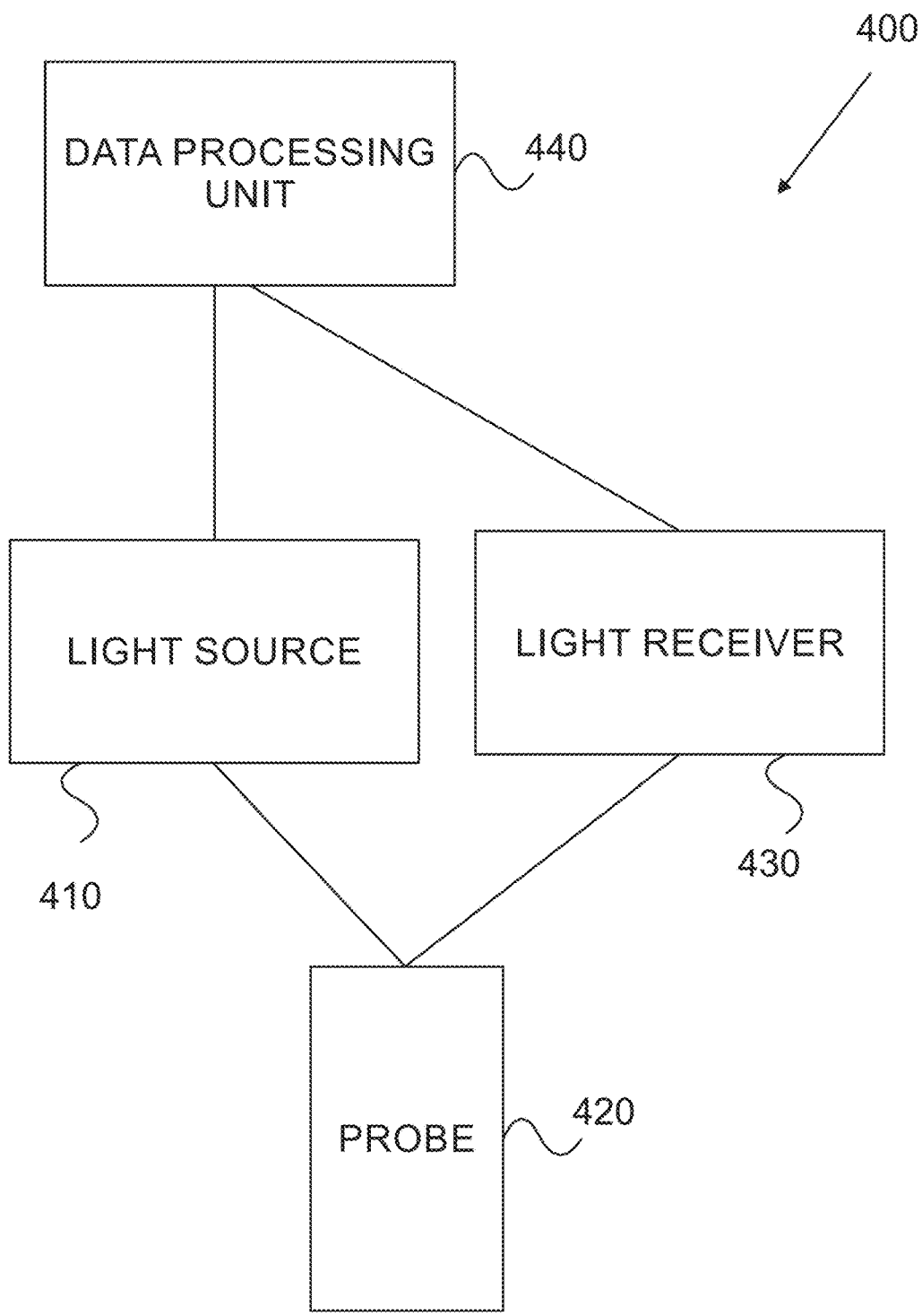
FIG. 4 illustrates a system according to an example.

FIG. 4 shows an example of a system 400. What is said above regarding the method 300 applies accordingly also to the system and the system can be configured accordingly. The system can be provided as a light-activated drug delivery system.

The system 400 may comprise a light source 410, such as a laser source, which may be configured for providing light signals for actuating and/or monitoring drug delivery. The system may also comprise an optical probe 420, such as an optical fiber, coupled to the light source for transmitting the light signals to a tissue for actuating and/or monitoring drug delivery and for transmitting light signals from the tissue for monitoring the drug delivery. The system may comprise a light receiver 430 coupled to the optical probe for receiving the light signals from the tissue for monitoring the drug delivery. The system may be configured for multi-phase drug delivery with two or more sequential actuation and/or monitoring phases. For the drug delivery, the drug-deliver construct 100 may be used, for example. The system may also be configured for causing a first light signal having a first wavelength to be transmitted through the optical probe to or from the tissue for actuating and/or monitoring the drug delivery. The system may be configured for causing a second light signal having a second wavelength to be transmitted, simultaneously with the first light signal, through the optical probe to or from the tissue for actuating and/or monitoring the drug delivery. Here, the first wavelength can be different from the second wavelength.

The system 400 may comprise one or more couplers, which may be fiber couplers, such as passive two-way fiber couplers. Each of the one or more couplers may be configured for simultaneously coupling the optical probe 420, such as an optical fiber, to the light source 410 for transmitting one or more first downstream light signals from the light source to the optical delivery probe and to the light receiver 430 for transmitting one or more first upstream light signals from the optical probe to the light receiver. The couplers can thus be separate so that each coupler is dedicated to its own probe. Each coupler and each probe may provide a separate measurement channel for the system. The system 400 may comprise or be coupled to a data processing unit 440. The data processing unit may be coupled to the light source 410 and/or the light receiver 430 for receiving and/or transmitting information regarding the drug delivery. It may, for example, provide information for controlling, manually or automatically, one or more parameters of the light source for transmitting the light signals for the drug delivery. It may also receive information from the light receiver, which information may be utilized for controlling the one or more parameters of the light source. The data processing unit may be configured to collect data from the drug delivery. It may also be configured to analyze data for the drug delivery. It may be configured to delivers guidance for the operation of the drug delivery. Any or all of these may be performed locally and/or remotely. The data processing unit may thus be a local and/or a remote data processing unit, such as a cloud processing unit. It may also utilize distributed computing to perform any of its actions locally and/or remotely. The data processing unit may also be external to the system, so that the system may be communicatively connected to the data processing unit.

The system 400 may comprise a wavelength-sensitive detection unit for simultaneously monitoring two or more different wavelengths received through the optical probe 420 for monitoring drug delivery. The detection unit may be part of the light-receiver 430. The detection unit may provide monitoring information to the data processing unit.

The system 400 may optionally comprise a drug delivery unit for delivering the drug to a subject, for example utilizing the drug-delivery construct 100 as disclosed herein. The drug delivery unit may be configured for adjusting the dosage of the drug, for example automatically. For this purpose, information from the data processing unit 440 may be used, manually and/or automatically.

A particular solution has a system 400 comprising a signal processing unit such as a cloud-connected personal computer (PC), a controller such as a laser and shutter controller, a light receiver (which may comprise one or more spectrometers and/or photodetectors), a light source (which may comprise one or more laser modules) and one or more couplers.

One or more channels with individual laser modules may be coupled through a coupler, such as a lens coupler, into light delivery probe such as an application fiber. Light coming back from the probe can be collected through a coupler, such as a fiber coupler. Here, the lens coupler and the fiber coupler can now be integrated as a single two-way coupler, where a first path is for the downstream light signals from the light source 410 to the optical probe 420 and the second path is for the upstream light signals from the optical probe to the light receiver 430.

Figure 2A:
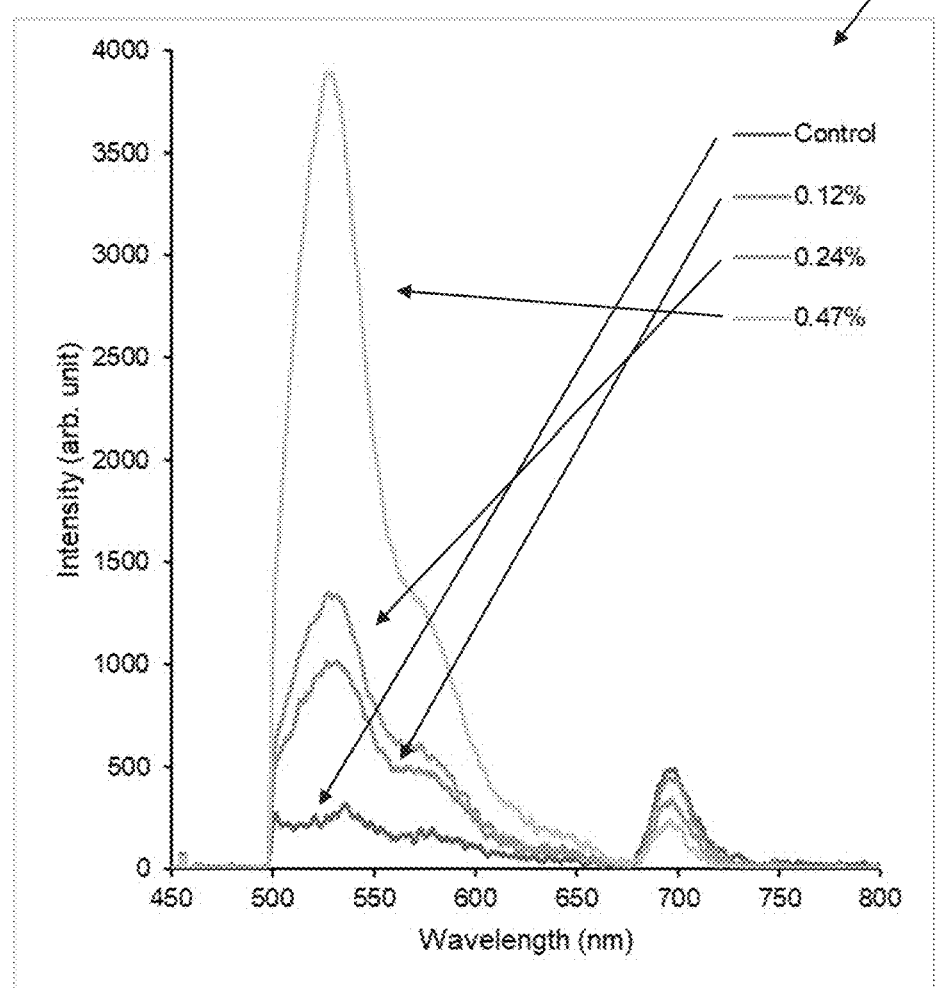
FIGS. 2a-c illustrate test results according to an example.
Figure 2B:
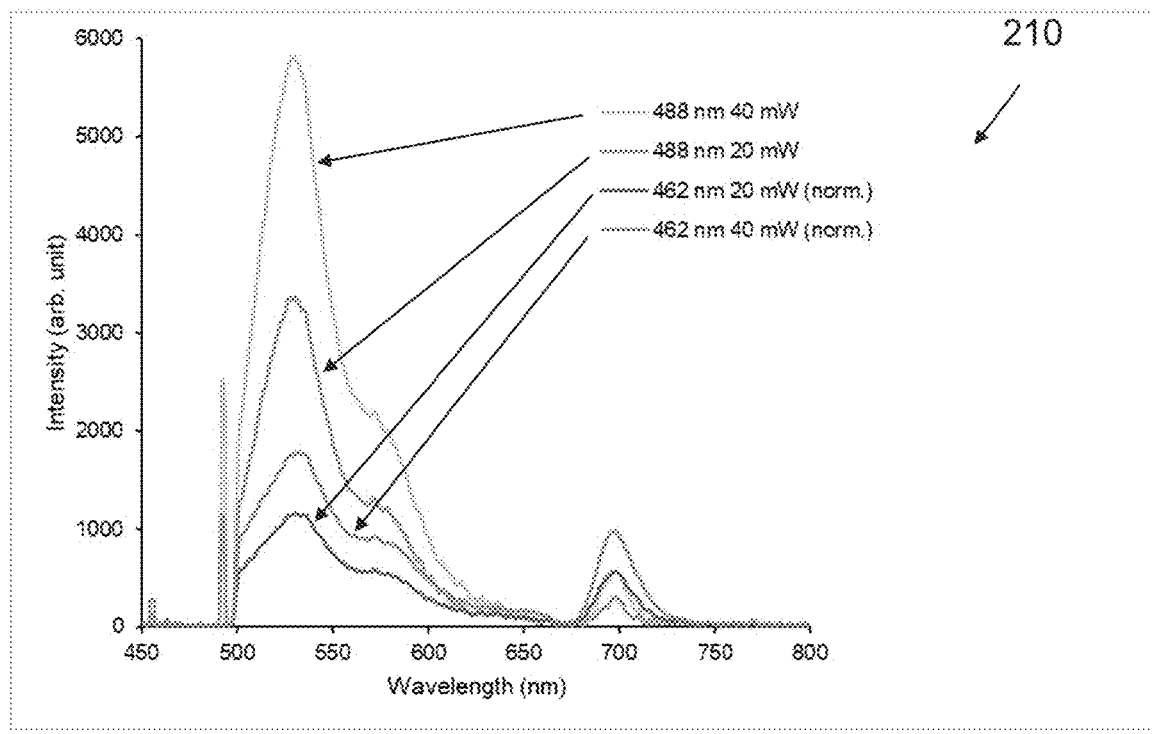
Figure 2C:
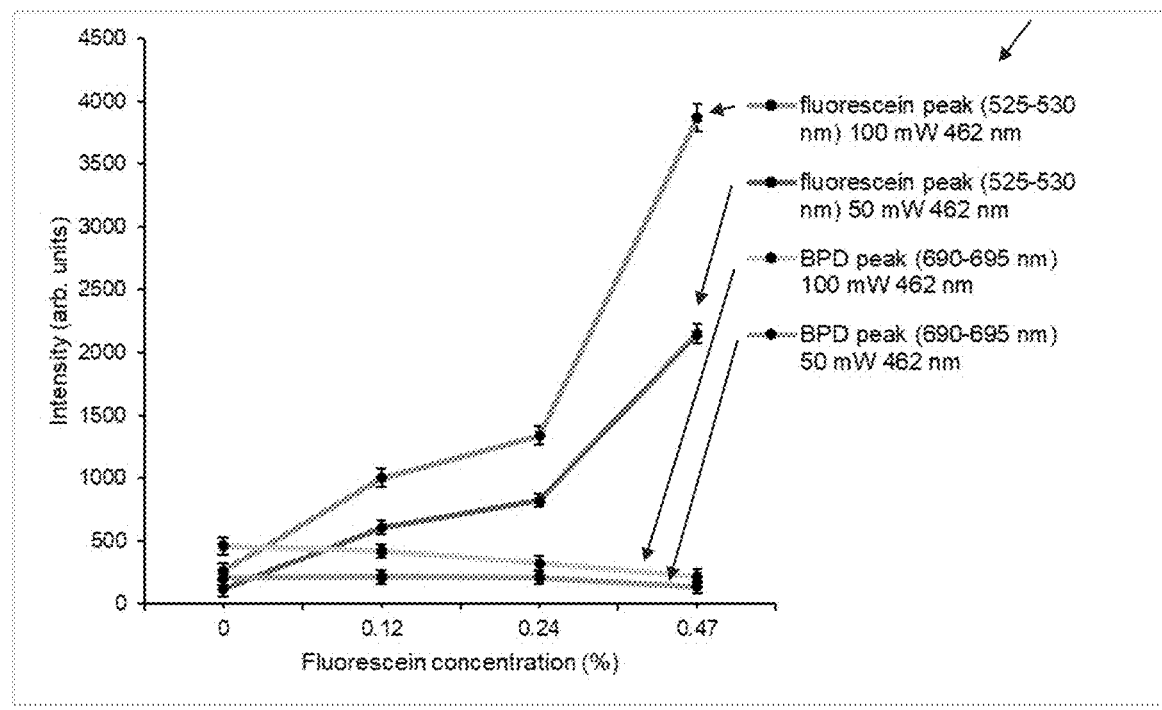

FIGS. 2*a*-*c* show an example of test results. FIG. 2*a* illustrates a possible dependence of fluorescence label proportion (%) vs. fluorescence intensity. FIGS. 2*b* and 2*c* illustrate a possible dependence of the fluorescence signal ratio from a photosensitizer (BPD at 700 nm) and fluorescence label (fluorescein at 520 nm) on illumination wavelength and power.

In general, the present solutions allow monitoring multiple different processes related to drug delivery, release from the carrier and activation of the drug including, but not restricted, to any of the following alone or in any combination.

Confirming drug carrier presence in the tissue prior to the treatment, for example utilizing fluorescence of the drug-delivery construct.

Monitoring the integrity of the drug-delivery construct, for example through a ratio between fluorescence peaks from different components of the drug delivery construct. For example, benzoporphyrin derivative (BPD) can be part of PICs on the liposomal surface and fluorescein dye can be incorporated into liposomal bilayer. The BPD-fluorescein emission signal ratio can be used for monitoring integrity of the drug-delivery construct. For example, PICs detaching from the surface of the drug-delivery construct due to changes in microenvironment or any internal or external trigger, can cause drop in the BPD-fluorescein emission intensity ratio. Also, a change in the fluorescence of the encapsulated drug (fluorescence unquenching) can give indication that there has been a disruption in the envelope integrity and consequent full or partial drug release.

Inducing release of one or more drugs, like chemotherapeutic drugs, from the drug-delivery construct.

Monitoring release of one or more drugs from the drug-delivery construct, for example by evaluating increase in fluorescence of the one or more drugs. This may be based on fluorescence unquenching and/or envelope integrity deterioration.

Inducing photodynamic reaction by activation of a photosensitizer.

Monitoring photodynamic treatment progress in real-time by decrease in photosensitizer fluorescence. Accordingly, photobleaching may be utilized.

Verifying, possibly in real time, that treatment light reaches the (target) tissue at sufficient level and adjust the light parameters in case light signal is not optimal and/or changes at any point during treatment. This allows adjusting for tissue optical properties changing during the course of illumination. This also allows decreasing the risk of under- or over-treatment.

Monitoring, possibly in real time, light propagation in tissue by measuring light transmission between two interstitial optical probes, such as optical fibers.

Verifying that one or more drugs have been consumed in the illumination, for example if no fluorescence present. This may facilitate making treatment result independent of tissue variations.

Having multiple optical probes, for example acting as point sources of light to the tissue, allows fluorescence monitoring and/or treatment at any desired location or locations even over a large area by placing the optical probes to desired locations. Alternatively or additionally, the optical probes can be clustered on a varying density grid based on the local tissue properties to optimize treatment illumination and/or monitoring. The disclosed solutions allow also monitoring and/or treatment where multiple dyes and/or photosensitizers are used simultaneously to combine their benefits. For example, BPD may allow better tumor penetration depth of light (activation at 690 nm), while 5-ALA (5-aminolevulinic acid, activation at 635 nm) may provide an improved fluorescence monitoring capability. With the disclosed solutions both dyes can be activated and/or monitored simultaneously, for example in real time. The system may be configured to activate fluorescence emission of several dyes and/or photosensitizers simultaneously with one wavelength, for example if the absorption spectra overlap the excitation wavelength. This can be achieved by having a wavelength-sensitive detection unit for each monitoring channel. This allows simplifying the design and hardware requirements of the system since only one laser is needed. In this case, emission peaks of the excited dyes may be analyzed from the device screen, external display, and/or a computer where the spectral data is fed. Fluorescence emission peaks can be visualized by collecting and analyzing the data from the wavelength-sensitive detection unit.

The system can also be configured for utilizing several fluorescence excitation wavelengths to activate targets which may include any of the following alone or in any combination: dyes, fluorescence labels and/or photosensitizers. This may be done simultaneously, sequentially in any desired sequence and/or at different points in time. This can be done utilizing filters for selectively activating the targets by selecting activation wavelength for each target so that it does not significantly overlap with absorption windows of other targets being used. The fluorescence properties of the target, such as a photosensitizer, can be used for monitoring the location, distribution, and/or accumulation using low-energy excitation wavelength(s) without generating significant PDT or other drug activation effects. A laser, such as a high-power laser, at same or different excitation wavelength can then be used to activate the PDT effect from the photosensitizer when it has been detected by fluorescence to be accumulated into the tissue, such as a tumor tissue.

Disclosed is a system and method of activation and/or monitoring of multi-phase photo-activated drug delivery. It may be adapted for cancer treatment or any other similar treatment process. The treatment may comprise one or more of the following phases, in any combination, possibly in varying order:

Giving the drug delivery construct to a patient, for example via IV (intravenously) or IP (intraperitoneally).

Inserting one or more treatment and/or monitoring optical probes, which may be non-invasive, to a tissue to be treated, such as a tumor.

Illuminating the tissue, for example sequentially, with the probe(s) and measuring optical signal at the same wavelength with other probe(s) to determine uniform illumination field within the tissue for one or more selected wavelengths for treatment and/or monitoring.

Illuminating the tissue with a selected wavelength that can be absorbed by one or more fluorescent parts, such as a photosensitizer (PS), a dye or a drug, and measuring the fluorescence response in the tissue at one or more wavelengths to determine whether the drug-delivery construct, or the carrier, is present in the tissue and/or at the desired concentration. This may include multiple measurements to determine relative change in tissue and saturation level for starting the treatment.

Illuminating the tissue with one or more wavelengths that dissolves the drug delivery construct and releases the drug(s) to the tissue. This may involve monitoring, at the same time or in between or after, the fluorescence signal change of the drug-delivery construct, and/or the drug(s) thereof, to identify completion of drug release.

Illuminating the tissue with one or more wavelengths to photo-activate a drug and/or photosensitizer and/or to boost a drug efficacy by light. This may involve monitoring the change in a fluorescence signal (or photobleaching) from one or more activated targets to monitor progress of the activation process.

Monitoring an optical response from the tissue between different probes during the process to detect possible abnormalities like bleeding and/or tissue darkening and/or ablation.

Informing, for example via a graphical user interface (GUI), the user about progress of the drug deliver, for example about a success level and/or completion of different phases, about stopping the process when all the drug is released and/or activated, or if the drug was not detected in the tissue, and/or if a complication is detected in the treatment and/or any other abnormal incident Collecting data from the operation parameters and/or monitoring signals to a data storage locally or remotely to allow local and/or remote analysis of the data, for example by an experienced user and/or machine learning and/or AI algorithm. This can be done to determine any of progress, length, continuation or success of the different phases during the treatment, for example based on earlier data from similar treatments and/or treatment planning data.

The system as described above may be implemented in software, hardware, application logic or a combination of software, hardware and application logic. The application logic, software or instruction set may be maintained on any one of various conventional computer-readable media. A "computer-readable medium" may be any media or means that can contain, store, communicate, propagate or transport the instructions for use by or in connection with an instruction execution system, apparatus, or device, such as a computer. A computer-readable medium may comprise a computer-readable storage medium that may be any media or means that can contain or store the instructions for use by or in connection with an instruction execution system, apparatus, or device, such as a computer. The examples can store information relating to various processes described herein. This information can be stored in one or more memories, such as a hard disk, optical disk, magneto-optical disk, RAM, and the like. One or more databases can store the information used to implement the embodiments. The databases can be organized using data structures (e.g., records, tables, arrays, fields, graphs, trees, lists, and the like) included in one or more memories or storage devices listed herein. The databases may be located on one or more devices comprising local and/or remote devices such as servers. The processes described with respect to the embodiments can include appropriate data structures for storing data collected and/or generated by the processes of the devices and subsystems of the embodiments in one or more databases.

All or a portion of the embodiments can be implemented using one or more general purpose processors, micropro- cessors, digital signal processors, micro-controllers, and the like, programmed according to the teachings of the embodi- ments, as will be appreciated by those skilled in the computer and/or software art(s). Appropriate software can be readily prepared by programmers of ordinary skill based on the teachings of the embodiments, as will be appreciated by those skilled in the software art. In addition, the embodiments can be implemented by the preparation of application-specific integrated circuits or by interconnecting an appropriate network of conventional component circuits, as will be appreciated by those skilled in the electrical art(s). Thus, the embodiments are not limited to any specific combination of hardware and/or software.

The different functions discussed herein may be performed in a different order and/or concurrently with each other.

Any range or device value given herein may be extended or altered without losing the effect sought, unless indicated otherwise. Also any example may be combined with another example unless explicitly disallowed.

Although the subject matter has been described in language specific to structural features and/or acts, it is to be understood that the subject matter defined in the appended claims is not necessarily limited to the specific features or acts de-scribed above. Rather, the specific features and acts described above are disclosed as examples of implementing the claims and other equivalent features and acts are intended to be within the scope of the claims.

It will be understood that the benefits and advantages described above may relate to one embodiment or may relate to several embodiments. The embodiments are not limited to those that solve any or all of the stated problems or those that have any or all of the stated benefits and advantages. It will further be understood that reference to 'an' item may refer to one or more of those items.

The term 'comprising' is used herein to mean including the method, blocks or elements identified, but that such blocks or elements do not comprise an exclusive list and a method or apparatus may contain additional blocks or elements.

Numerical descriptors such as 'first', 'second', and the like are used in this text simply as a way of differentiating between parts that otherwise have similar names. The numerical descriptors are not to be construed as indicating any particular order, such as an order of preference, manufacture, or occurrence in any particular structure.

Although the disclosed embodiments have been the described in conjunction with a certain type of apparatus and/or method, the disclosed embodiments is not limited to any certain type of apparatus and/or method. While the present disclosure have been described in connection with a number of examples, embodiments and implementations, the present disclosure are not so limited, but rather cover various modifications, and equivalent arrangements, which fall within the purview of the claims. Although various examples have been described above with a certain degree of particularity, or with reference to one or more individual embodiments, those skilled in the art could make numerous alterations to the disclosed examples without departing from the scope of this specification.

The invention claimed is:

1. A method for light-activated drug delivery, the method comprising:
coupling an optical probe to a tissue for transmitting light signals to the tissue for actuating and monitoring drug delivery;

wherein the method is a multi-phase method for drug delivery having two or more sequential actuation and monitoring phases for the drug delivery, the method comprising:

causing a first light signal having a first wavelength to be transmitted through the optical probe for actuating the drug delivery; and causing a second light signal having a second wavelength to be transmitted, simultaneously with the first light signal, through the optical probe for monitoring the drug delivery, the first wavelength being different from the second wavelength.

2. The method according to claim 1, wherein the first light signal is transmitted to the tissue and the second light signal is received from the tissue to monitor the arrival of a drug to the tissue.

3. The method according to claim 1, wherein the first light signal is transmitted to the tissue and the second light signal is received from the tissue to monitor the integrity of a carrier encapsulating a drug for drug delivery.

4. The method according to claim 1, wherein the first light signal is transmitted to the tissue to actuate the drug delivery by inducing a release of a drug from a carrier and the second light signal is received from the tissue to monitor the release.

5. The method according to claim 1, wherein the first light signal is transmitted to the tissue to actuate the drug delivery by inducing an activation of a drug and the second light signal is received from the tissue to monitor the activation.

6. The method according to claim 1, wherein the first light signal is transmitted to the tissue for probing an activation of a drug and the second light signal is received from the tissue for monitoring a completion of the activation of a drug.

7. The method according to claim 1, wherein the first light signal is transmitted to the tissue to activate fluorescence from a drug and/or a drug-delivery construct encapsulating the drug and the second light signal is received from the tissue to monitor the fluorescence.

8. The method according to claim 1, wherein the first light signal is transmitted to the tissue to activate characteristic optical response, like fluorescence, reflectance or Raman scattering signal or alike, from the tissue and the second light signal is received from the tissue to monitor the characteristic optical response.

9. The method according to claim 1, comprising causing one or more signals having a different wavelength to be transmitted simultaneously with the first signal and the second signal through the optical probe for actuating and/or monitoring the drug delivery, the different wavelength being different from the first wavelength and the second wavelength.

10. The method according to claim 1, wherein two or more different wavelengths are used for actuating drug delivery and/or two or more different wavelengths are used for inducing a monitoring signal.

11. The method according to claim 1, wherein two or more different wavelengths are used for monitoring drug delivery.

12. A light-activated drug delivery system comprising:
a light source for providing light signals for actuating and monitoring drug delivery;
an optical probe coupled to the light source for transmitting the light signals to a tissue for actuating and monitoring drug delivery and for transmitting light signals from the tissue for monitoring the drug delivery; and
a light receiver coupled to the optical probe for receiving the light signals from the tissue for monitoring the drug delivery;
wherein the system is configured for multi-phase drug delivery with two or more sequential actuation and/or monitoring phases and for:
causing a first light signal having a first wavelength to be transmitted through the optical probe for actuating the drug delivery; and
causing a second light signal having a second wavelength to be transmitted, simultaneously with the first light signal, through the optical probe for monitoring the drug delivery, the first wavelength being different from the second wavelength.

13. The system according to claim 12, configured to monitor an arrival of a drug to the tissue by transmitting the first light signal to the tissue and receiving the second light signal from the tissue.

14. The system according to claim 12, configured to monitor the integrity of a carrier encapsulating a drug for drug delivery by transmitting the first light signal to the tissue and receiving the second light signal from the tissue.

15. The system according to claim 12, configured to:
actuate the drug delivery by transmitting the first light signal to the tissue to induce a release of a drug from a carrier, and
receive the second light signal from the tissue to monitor the release.

16. The system according to claim 12, configured to:
actuate the drug delivery by transmitting the first light signal to the tissue to induce an activation of a drug, and
receive the second light signal from the tissue to monitor the activation.

17. The system according to claim 12, configured to monitor completion of activation of a drug by transmitting the first light signal to the tissue and receiving the second light signal from the tissue.

18. The system according to claim 12, configured to monitor the drug delivery by:
transmitting a first light signal to the tissue to activate fluorescence from a drug and/or a drug-delivery construct, and
receiving the second light signal to monitor the fluorescence.

19. The system according to claim 12, configured to monitor a characteristic optical response from the tissue by:
transmitting a first light signal to the tissue to induce a characteristic optical response, like fluorescence, reflectance or Raman scattering signal, from the tissue, and
receiving the second light signal to monitor the characteristic optical response from the tissue.

20. The system according to claim 12, configured for causing one or more signals having a different wavelength to be transmitted simultaneously with the first signal and the second signal through the optical probe for actuating and/or monitoring the drug delivery, the different wavelength being different from the first wavelength and the second wavelength.

* * * * *